US009956288B2

(12) United States Patent
Henke et al.

(10) Patent No.: US 9,956,288 B2
(45) Date of Patent: *May 1, 2018

(54) HIGHLY CONCENTRATED STABLE MELOXICAM SOLUTIONS

(71) Applicant: Boehringer Ingelheim Vetmedica GmbH, Ingelheim am Rhein (DE)

(72) Inventors: Stefan Henke, Kirchen (DE); Bernd Kruss, Hochdorf (DE); Bernhard Hassel, Ockenheim (DE); Hans-Juergen Kroff, Schoeneberg (DE); Martin A. Folger, Ingelheim am Rhein (DE); Klaus Daneck, Biberach an der Riss (DE); Axel Prox, Warthausen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/297,594

(22) Filed: Oct. 19, 2016

(65) Prior Publication Data

US 2017/0035885 A1   Feb. 9, 2017

Related U.S. Application Data

(60) Division of application No. 13/803,008, filed on Mar. 14, 2013, now abandoned, which is a continuation of application No. 11/290,933, filed on Nov. 30, 2005, which is a continuation of application No. 09/860,737, filed on May 18, 2001, now abandoned.

(60) Provisional application No. 60/216,004, filed on Jul. 3, 2000.

(30) Foreign Application Priority Data

Jun. 20, 2000   (DE) ................... 100 30 345

(51) Int. Cl.

| A61K 31/33 | (2006.01) |
|---|---|
| A61K 47/18 | (2017.01) |
| A61K 9/00 | (2006.01) |
| A61K 31/5415 | (2006.01) |
| A61K 45/06 | (2006.01) |
| A61K 47/10 | (2017.01) |
| A61K 47/26 | (2006.01) |

(52) U.S. Cl.

CPC .......... *A61K 47/183* (2013.01); *A61K 9/0019* (2013.01); *A61K 9/0095* (2013.01); *A61K 31/5415* (2013.01); *A61K 45/06* (2013.01); *A61K 47/10* (2013.01); *A61K 47/26* (2013.01)

(58) Field of Classification Search
CPC .. A61K 47/183; A61K 9/0019; A61K 9/0095; A61K 31/5415; A61K 45/06; A61K 47/10; A61K 47/26

See application file for complete search history.

(56) References Cited

U.S. PATENT DOCUMENTS

| 2,795,529 | A | | 6/1957 | Alburn et al. | |
|---|---|---|---|---|---|
| 3,089,818 | A | * | 5/1963 | Stone .................. | A61K 9/146 252/363.5 |
| 4,233,299 | A | | 11/1980 | Trummlitz et al. | |
| 4,447,443 | A | * | 5/1984 | Goldenberg ......... | A61K 31/415 514/400 |
| 4,482,554 | A | | 11/1984 | Gebhardt et al. | |
| 4,628,053 | A | * | 12/1986 | Fries .................... | A61K 9/0019 514/226.5 |
| 4,748,174 | A | | 5/1988 | Veronesi | |
| 4,794,117 | A | | 12/1988 | Corbiere | |
| 5,026,560 | A | | 6/1991 | Makino et al. | |
| 5,169,847 | A | * | 12/1992 | Nagy nee Kricsfalussy ........ | A61K 9/0019 514/226.5 |
| 5,283,065 | A | | 2/1994 | Doyon et al. | |
| 5,700,816 | A | | 12/1997 | Isakson et al. | |
| 6,046,191 | A | | 4/2000 | Hamley et al. | |
| 6,106,862 | A | | 8/2000 | Chen et al. | |
| 6,166,012 | A | | 12/2000 | Muller et al. | |
| 6,183,779 | B1 | | 2/2001 | Ouali et al. | |
| 6,184,220 | B1 | | 2/2001 | Turck et al. | |
| 6,187,800 | B1 | | 2/2001 | Suri et al. | |
| 6,221,377 | B1 | | 4/2001 | Meyer | |
| 6,495,603 | B1 | | 12/2002 | Miyake et al. | |
| 6,682,747 | B1 | | 1/2004 | Turck et al. | |

(Continued)

FOREIGN PATENT DOCUMENTS

| AU | 673675 B2 | 11/1996 |
|---|---|---|
| AU | 762464 B2 | 6/2003 |

(Continued)

OTHER PUBLICATIONS

Stei et al ( Br J Rheumatol, 1996, 35(1), 44-5).*
Gerard (WO9301814, published Apr. 2, 1993, Machine Translation used for this Office Action).*
Hermann (WO9809654, published Dec. 3, 1998, Machine Translation used for this Office Action).*
Gerard (WO9301814, published Apr. 2, 1993, Machine Translation).*
Hermann (WO9809654, published Dec. 3, 1998, Machine Translation).*
Rolfe et al (Bioscience Reports, 1997, 17(1), 9-16).*
Stei (Br J Rheumatol, 1996, 35(1), 44-5).*

(Continued)

*Primary Examiner* — Rachael Bredefeld
*Assistant Examiner* — Ibrahim D Bori
(74) *Attorney, Agent, or Firm* — Marc Began; Judy Jarecki-Black

(57) ABSTRACT

Aqueous cyclodextrin-free solution of meloxicam for administration by oral or parenteral route, containing a pharmacologically acceptable meloxicam salt of an organic or inorganic base and one or more suitable excipients, the content of dissolved meloxicam salt being more than 10 mg/mL. The solution is for treating a mammal suffering from one or more of pain, inflammation, fever, acute mastitis, diarrhea, lameness, locomotor deficiency, or respiratory illness.

4 Claims, No Drawings

(56) References Cited

U.S. PATENT DOCUMENTS

| | | |
|---|---|---|
| 6,869,948 B1 | 3/2005 | Bock et al. |
| 7,105,512 B2 | 9/2006 | Morizono et al. |
| 8,920,820 B2 | 12/2014 | Folger et al. |
| 2001/0055569 A1 | 12/2001 | Davis et al. |
| 2002/0016342 A1 | 2/2002 | Scolnick et al. |
| 2002/0035107 A1 | 3/2002 | Henke et al. |
| 2002/0077328 A1 | 6/2002 | Hassan et al. |
| 2002/0099049 A1 | 7/2002 | Burch et al. |
| 2002/0131998 A1 | 9/2002 | Martani |
| 2003/0109701 A1 | 6/2003 | Coppi et al. |
| 2003/0119825 A1 | 6/2003 | Folger et al. |
| 2003/0199482 A1 | 10/2003 | Seibert et al. |
| 2004/0001883 A1 | 1/2004 | Matsui et al. |
| 2004/0015126 A1 | 1/2004 | Zierenberg et al. |
| 2004/0037869 A1 | 2/2004 | Cleverly et al. |
| 2004/0043992 A1 | 3/2004 | Tolba et al. |
| 2004/0170687 A1 | 9/2004 | Hurd et al. |
| 2004/0171611 A1 | 9/2004 | Trummlitz et al. |
| 2004/0180092 A1 | 9/2004 | Henke et al. |
| 2004/0198826 A1 | 10/2004 | Baiker et al. |
| 2004/0214753 A1 | 10/2004 | Britten et al. |
| 2004/0229038 A1 | 11/2004 | Cooper et al. |
| 2004/0234596 A1 | 11/2004 | Ohki et al. |
| 2004/0253312 A1 | 12/2004 | Sowden et al. |
| 2005/0038018 A1 | 2/2005 | Kanbe et al. |
| 2005/0147664 A1 | 7/2005 | Liversidge et al. |
| 2005/0187212 A1 | 8/2005 | Ohki et al. |
| 2005/0187213 A1 | 8/2005 | Lang et al. |
| 2005/0197332 A1 | 9/2005 | Altman |
| 2005/0244491 A1 | 11/2005 | Ohki et al. |
| 2005/0245510 A1 | 11/2005 | Friton et al. |
| 2005/0277634 A1 | 12/2005 | Janott et al. |
| 2005/0288280 A1 | 12/2005 | Friton et al. |
| 2006/0160793 A1 | 7/2006 | Altman |
| 2006/0217431 A1 | 9/2006 | Daemmgen et al. |
| 2007/0077296 A1 | 4/2007 | Folger et al. |
| 2007/0099907 A1 | 5/2007 | Altman |
| 2008/0132493 A1 | 6/2008 | Folger et al. |
| 2008/0234380 A1 | 9/2008 | Shapiro |
| 2008/0280840 A1 | 11/2008 | Lang et al. |
| 2010/0233399 A1 | 9/2010 | Pradella et al. |
| 2011/0083985 A1 | 4/2011 | Folger et al. |
| 2011/0275618 A1 | 11/2011 | Folger et al. |
| 2013/0178467 A1 | 7/2013 | Henke et al. |
| 2014/0066440 A1 | 3/2014 | Folger et al. |
| 2014/0113893 A1 | 4/2014 | Folger et al. |
| 2014/0179639 A1 | 6/2014 | Lang et al. |
| 2014/0332438 A1 | 11/2014 | Henke et al. |
| 2015/0051198 A1 | 2/2015 | Folger et al. |

FOREIGN PATENT DOCUMENTS

| | | | |
|---|---|---|---|
| CA | 2164100 A1 | 1/1995 | |
| CA | 2166204 A1 | 1/1995 | |
| CA | 2264626 A1 | 3/1998 | |
| CA | 2326048 A1 | 10/1999 | |
| CA | 2326517 A1 | 10/1999 | |
| CA | 2404360 A1 | 9/2001 | |
| CA | 2414063 A1 | 12/2001 | |
| CA | 2469588 | 6/2003 | |
| CA | 2503396 A1 | 5/2004 | |
| CN | 1546033 A | 11/2004 | |
| DE | 4217971 C1 | 10/1993 | |
| DE | 19729879 A1 | 1/1999 | |
| DE | 10010123 A1 | 9/2001 | |
| EP | 0093999 A2 | 11/1983 | |
| EP | 0177870 A2 | 4/1986 | |
| EP | 0945134 A1 | 9/1999 | |
| EP | 1568369 A1 | 8/2005 | |
| ES | 2065846 A1 | 2/1995 | |
| GB | 2455875 A | 6/2009 | |
| IT | 1251650 B | 5/1995 | |
| JP | 2003535902 A | 12/2003 | |
| WO | 199301814 A1 | 2/1993 | |
| WO | 1996041625 A1 | 12/1996 | |
| WO | 1998009654 A1 | 3/1998 | |
| WO | WO 9850045 A1 * | 11/1998 | ............ A61K 31/65 |
| WO | 1999059634 A1 | 11/1999 | |
| WO | 2001008689 A1 | 2/2001 | |
| WO | 2001037838 A1 | 5/2001 | |
| WO | 2001097813 A2 | 12/2001 | |
| WO | 2002041899 A1 | 5/2002 | |
| WO | 2002085331 A1 | 10/2002 | |
| WO | 2003082297 A1 | 10/2003 | |
| WO | 2005004915 A2 | 1/2005 | |
| WO | 2005079806 A1 | 9/2005 | |
| WO | 2005105101 | 11/2005 | |
| WO | 2006000306 A1 | 1/2006 | |
| WO | 2006015942 A1 | 2/2006 | |
| WO | 2006100213 A1 | 9/2006 | |
| WO | 2007039417 A1 | 4/2007 | |
| WO | 2007135505 A2 | 11/2007 | |
| WO | 2008113149 A2 | 9/2008 | |
| WO | 2011107150 A1 | 9/2011 | |
| WO | 2011107498 A1 | 9/2011 | |
| WO | 2011138197 A2 | 11/2011 | |

OTHER PUBLICATIONS

"Committee for Veterinary Medicinal Products Meloxicam (Extension to bovine milk) Summary Report (4)". The European Agency for the Evaluation of Medicinal Products, Veterinary Medicines Evaluation Unit, Jul. 1999, pp. 1-2. [Accessed at http://www.ema.europa.eu/docs/en_GB/document_library/Maximum_Residue_limits_-_Report/2009/11/WC500014953.pdf].

"Committee for Veterinary Medicinal Products—Meloxicam (Extension to PIGS)—Summary Report (5)". The European Agency for the Evaluation of Medicinal Products, Veterinary Medicines and Information Technology, Dec. 2000, pp. 1-3.

"MELOXICAM Veterinary—Systemic"., The United States Pharmacopeial Convention, 2004, pp. 1-9. [Accessed at http://vetmed.tamu.edu/common/docs/public/aavpt/meloxicam.pdf on Aug. 16, 2013].

"Metacam (R) 0.5 mg/ml oral suspension for cats." Boehringer Ingelheim Datasheet, WEB site: http://www.vetgb.com/vetgb_pdfs/metacamc_7a5c_vetgb.pdf> Accessed on Jun. 8, 2010.

"Metacam Professional Insert: Metacam® (meloxicam) 1.5 mg/mL Oral Suspension (equivalent to 0.05 mg per drop) Non-Steroidal anti-inflammatory drug for oral use in dogs only". Boehringer Ingelheim, Jan. 2005, 2 pages.

"Metacam(R)" FDA Animal & Veterinary Drug Labels, WEB site: http://www.fda.gov/downloads/AnimalVeterinary/Products/ApprovedAnimalDrugProducts/DrugLabels/UCM050397.pdf> Accessed Jun. 8, 2010.

"METACAM—Community register of veterinary medicinal products" accessed online at http://pharmacos.eudra.org/F2/register/v004.htm, 2005.

Abstract in English for IT1251650, 1995.

Bednarek et al., "Effect of steroidal and non-steroidal anti-imflammatory drugs in combination with long-acting oxytetracycline on non-specific immunity of calves suffering from enzootic bronchopneumonia". Veterinary Microbiology, vol. 96, 2003, pp. 53-67.

Bednarek et al., "The effect of steroidal and non-steroidal anti-inflammatory drugs on the cellular immunity of calves with experimentally-induced local lung inflammation". Veterinary Immunology and Immunopathology, vol. 71, 1999, pp. 1-15.

Boehringer Ingelheim; Metacam (Meloxicam) Now Approved for Pigs and Mastitis in Dairy Cows; May 2003 Press Release; pp. 1-2.

Farkouh et al., "Comparison of lumiracoxib with naproxen and ibuprofen in the Therapeutic Arthritis Research and Gastrointestinal Event Trial (TARGET), cardiovascular outcomes: randomised controlled trial". Lancet, vol. 364, Aug. 2004, pp. 675-684.

Fitzgerald et al., "COX-2 inhibitors and the cardiovascular system". Clinical and Experimental Rheumatology, vol. 19, No. 6, Supp. 25, Nov. 2001, pp. S31-S36.

Fitzpatrick et al., "Recognising and Controlling Pain and Inflammation in Mastitis". Proceedings of the British Mastitis Conference, Axient/Institute for Animal Health, Milk Development Council/Novartis Animal Health, 1998, pp. 36-44.

(56) References Cited

OTHER PUBLICATIONS

Gruet et al., "Bovine mastitis and intramammary drug delivery: review and perspectives". Advanced Drug Delivery Reviews, vol. 50, 2001, pp. 245-259.
International Search Report for PCT/EP2001/006904 dated Jan. 29, 2002.
Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.
Nell et al., "Comparison of vedaprofen and meloxicam in dogs with muskuloskeletal pain and inflammation". Journal of Small Animal Practice, vol. 43, No. 5, May 2002, pp. 208-212 [Accessed at http://www.ncbi.nlm.nih.gov/pubmed/12038853 on Sep. 27, 2013]. Abstract Only, 1 page.
Yamashita et al., "Effects of Carprofen and Meloxicam with or without Butorphanol on the Minimum Alveolar concentration of Sevoflurane in Dogs". The Journal of Veterinary Medical Science, Jan. 2008, pp. 29-35. [Accessed at https://www.jstage.jst.go.jp/article/jvms/70/1/70_1_20/_pdf on Mar. 5, 2014].
"Committee for Veterinary Medicinal Products Meloxicam Summary Report (1)". The European Agency for the Evaluation of Medicinal Products, Jun. 1997, pp. 1-7.

* cited by examiner

HIGHLY CONCENTRATED STABLE MELOXICAM SOLUTIONS

CROSS REFERENCE TO RELATED APPLICATIONS

This application is a divisional of U.S. Nonprovisional application Ser. No. 13/803,008, filed 14 Mar. 2013 and entitled "Highly Concentrated Stable Meloxicam Solutions", which is a continuation of U.S. Nonprovisional application Ser. No. 11/290,933, filed 30 Nov. 2005 and entitled "Highly Concentrated Stable Meloxicam Solutions," which is a continuation of U.S. Nonprovisional application Ser. No. 09/860,737, filed 18 May 2001 and entitled "Highly Concentrated Stable Meloxicam Solutions," which is a nonprovisional of U.S. Provisional Application No. 60/216,004, filed 3 Jul. 2000 and entitled "Highly Concentrated Stable Meloxicam Solutions," and which claims priority to German Application No. 100 30 345.5, filed 20 Jun. 2000. The disclosure of each aforementioned application is incorporated herein by reference in its entirety.

FIELD OF THE INVENTION

The present invention relates to highly concentrated stable meloxicam solutions for oral and parenteral administration, particularly for treating respiratory diseases in large farm animals.

BACKGROUND OF THE INVENTION

Meloxicam (4-hydroxy-2-methyl-N-(5-methyl-2-thiazolyl)-2H-1,2-benzothiazine-3-carboxamide-1,1-dioxide) is an active substance which belongs to the group of NSAIDs (non-steroidal antiinflammatory drugs). Meloxicam and the sodium and meglumine (N-methyl-D-glucamine) salt thereof are described in EP-A-0 002 482. EP-A-0 002 482 shows, inter alia, the example of a 0.2% injectable solution of meloxicam consisting of the meglumine salt of the active substance, sodium chloride, and water.

EP-A-0 945 134 discloses the pH-dependent solubility characteristics of meloxicam and its salts, i.e., the sodium salt, the ammonium salt, and the meglumine salt, in aqueous solution. According to EP-A-0 945 134, meloxicam is an active substance which does not dissolve readily in water and the meloxicam salts, particularly the meglumine salt, exhibit improved solubility as the pH increases between 4 and 10, as shown in Table 1 of EP-0 945 134. However, until now it has only been possible to produce stable, clear, aqueous solutions with a low concentration of meloxicam. In addition to involving the in situ formation of a meloxicam salt, e.g., meglumine salt, and the addition of solubilizers, these prior art solutions were required to have a pH in the range of maximum possible solubility as well as being reasonably well-tolerated and contain a high proportion of organic solvent. Formulation tests with the same or a similar recipe led to cloudiness of the solution if the meloxicam concentrations were higher, e.g., 2%.

WO9959634 A1 describes an eye drop solution containing 0.5% meloxicam but makes no reference to possible meloxicam concentrations over 1%. For example, a commercially available 0.5% meloxicam solution is used in small animals such as dogs, heifers, and calves to treat respiratory diseases.

Thus, it has not hitherto been possible to treat large farm animals with an injectable meloxicam solution as the low concentration of active substance in the injectable solution did not allow an acceptable, well-tolerated injection volume due to the great weight of the animals. Furthermore, parenteral administration requires that the solution be free from particles; if there are particles in a parenteral drug, there is a risk of vascular damage or embolism. Moreover, organic solvents, solubilizers, and water-soluble substances can only be used in certain concentrations to achieve acceptable drug tolerance. These problems are solved by the present invention which provides particle-free, highly concentrated meloxicam solutions which are stable over long periods and suitable for treating farm animals up to 750 kg in weight. The meloxicam solutions of the present invention should, therefore, be suitable for administration both orally or parenterally.

DETAILED DESCRIPTION OF THE INVENTION

Surprisingly, it has been found that highly concentrated meloxicam solutions which contain, in addition to a meloxicam salt and certain excipients, another excipient selected from among citric acid, lecithin, gluconic acid, tartaric acid, phosphoric acid, and EDTA or the salts thereof, may be produced so as to be particle-free and stable over long periods. The stability was achieved with an unexpectedly small amount of organic solubilizers. The formulation was found to be stable even when subjected to the process of final sterilization.

This results in the solution to the problem according to the invention, as a formulation of a meloxicam solution which contains, in addition to a meloxicam salt, small concentrations of solubilizer, a preservative, a buffer substance for achieving the optimum pH range, and another excipient.

The invention relates to aqueous cyclodextrin-free solutions of meloxicam for parenteral or oral administration which contain a pharmacologically acceptable meloxicam salt of an organic or inorganic base in a highly concentrated solution with 11-25 mg/mL of meloxicam together with suitable excipients.

The formulation according to the invention overcomes the problem arising from the prior art of providing an injectable solution of the active substance meloxicam which is also suitable for treating large farm animals, by permitting a high concentration of active substance in a particle free solution which is stable over the long term, having the composition described hereinafter.

The formulation according to the invention may contain, as the meloxicam salt, the meglumine, sodium, potassium, or ammonium salt, preferably the meloxicam meglumine salt.

The solubilizers used may be, for example, polyethyleneglycols, polyoxyethylene-polyoxypropylene copolymers (e.g., Poloxamer 188), glycofurol, arginine, lysine, castor oil, propyleneglycol, solketal, polysorbate, glycerol, sorbitol, mannitol, xylitol, polyvinylpyrrolidone, lecithin, cholesterol, 12-hydroxystearic acid-PEG660-ester, propyleneglycol monostearate, polyoxy-40-hydrogenated castor oil, polyoxyl-10-oleyl-ether, polyoxyl-20-cetostearylether, and polyoxyl-40-stearate or a mixture of sorbitol, mannitol and xylitol, preferably polyethyleneglycols, polyoxyethylene-polyoxypropylene copolymers, glycofurol, polyvinylpyrrolidone, lecithin, cholesterol, 12-hydroxystearic acid-PEG66O-esters, propyleneglycol monostearate, polyoxy-40-hydrogenated castor oil, polyoxyl-10-oleyl-ether, polyoxyl-20-cetostearylether, and polyoxyl-40-stearate. Particularly preferred are polyethyleneglycols, glycofurol, and polyoxyethylene-polyoxypropylene-copolymers, but especially polyethyleneglycols (e.g., Macrogol 300) and polyoxyethylene-polyoxypropylene copolymers (e.g., Poloxamer 188). The preservatives used may be, for example, ethanol, benzoic acid and the sodium or potassium salts thereof, sorbic acid and the sodium or potassium salts thereof, chlorobutanol, benzyl alcohol, phenylethanol, the methyl, ethyl, propyl, or butyl p-hydroxybenzoates, phenol, m-cresol, p-chloro-m-cresol, or benzalkonium chloride. Particularly preferred are ethanol, benzoic acid and the sodium or potassium salts thereof, sorbic acid and the sodium or potassium salts thereof, chlorobutanol, benzyl alcohol, phenylethanol, and the methyl, ethyl, propyl, or butyl p-hydroxybenzoates, but preferably ethanol, benzoic acid and the sodium or potassium salts thereof, sorbic acid and the sodium or potassium salts thereof, but especially ethanol.

The buffer system used to achieve a pH of between 8 and 10 may be, for example, glycine, a mixture of glycine and HCl, a mixture of glycine and sodium hydroxide solution, and the sodium and potassium salts thereof, a mixture of potassium hydrogen phthalate and hydrochloric acid, a mixture of potassium hydrogen phthalate and sodium hydroxide solution, or a mixture of glutamic acid and glutamate. Glycine, a mixture of glycine and HCl, and a mixture of glycine/sodium hydroxide solution, especially glycine, are particularly preferred.

Other suitable excipients are citric acid, lecithin, gluconic acid, tartaric acid, phosphoric acid, and EDTA or the alkali metal salts thereof, preferably tartaric acid and EDTA or the alkali metal salts thereof, particularly disodium EDTA.

One embodiment of the invention contains, in addition to the meglumine or sodium salt of meloxicam, polyethyleneglycols, glycofurol and/or polyoxyethylene-polyoxypropylene copolymers, but particularly polyethyleneglycols (e.g., Macrogol 300) and/or polyoxyethylene-polyoxypropylene copolymers (e.g., Poloxamer 188) as solubilizer, ethanol, benzoic acid and the sodium or potassium salts thereof, or sorbic acid and the sodium or potassium salts thereof, but particularly ethanol, as preservative, and glycine, a mixture of glycine/HCl, or a mixture of glycine/sodium hydroxide solution, but preferably glycine, as buffer, and disodium EDTA as an additional excipient.

The formulation according to the invention may contain meloxicam in a concentration of 11-25 mg/mL, preferably 13-24 mg/mL, preferably 16-23 mg/mL, particularly preferably 18-22 mg/mL, and especially 20 mg/mL.

The meglumine concentration may be between 12.5 and 16.5 mg/mL, preferably 13-16 mg/mL, preferably 13.5-15.5 mg/mL, more preferably 14-15 mg/mL, and especially about 14 mg/mL. The possible sodium, potassium, and ammonium concentrations are calculated accordingly.

The concentration of the solubilizers may be in the range from 20-200 mg/mL, preferably 30-150 mg/mL, preferably 40-130 mg/mL, more preferably 50-120 mg/mL, and especially 70-100 mg/mL.

The concentration of the preservative ethanol may be in the range from 100-200 mg/mL, preferably 120-180 mg/mL, and more preferably about 150 mg/mL.

The concentration of the preservatives benzoic acid and the sodium or potassium salts thereof, sorbic acid and the sodium or potassium salts thereof, chlorobutanol, benzyl alcohol, phenylethanol, phenol, m-cresol, and p-chloro-m-cresol, may be in the range from 0.5-50 mg/mL, preferably 1-10 mg/mL, and more preferably 3-5 mg/mL.

The concentration of the preservatives benzalkonium chloride, phenylmercury nitrate, and methyl, ethyl, propyl, or butyl-p-hydroxybenzoates, may be in the range from 0.01-4 mg/mL, preferably 0.02-3 mg/mL, and more preferably 0.1-0.5 mg/mL.

The concentration of the buffer substances may be between 4 and 50 mg/mL, preferably between 5 and 20 mg/mL, and more preferably between 8 and 10 mg/mL.

The concentration of the other excipients mentioned above, e.g., EDTA, citric acid, lecithin, gluconic acid, tartaric acid, and phosphoric acid or the salts thereof, may be in the range from 0.2-3 mg/mL, preferably 0.3-2.5 mg/mL, preferably 0.5-2 mg/mL, most preferably 0.6-1.5 mg/mL, and in particular 0.7-1.0 mg/mL.

Meglumine and meloxicam may be used in a molar ratio of between 9:8 and 12:8, preferably in a molar ratio of 11:8, but especially in a molar ratio of 10:8.

In the formulation according to the invention, meloxicam and the other excipient, particularly disodium EDTA, may be present in a weight ratio of between 25:1 and 15:1, preferably between 24:1 and 16:1, preferably between 23:1 and 17:1, more preferably between 22:1 and 18:1, most preferably between 21:1 and 19:1, and in particular about 20:1.

The formulation according to the invention may have shelf-life after opening of 28 days or more.

The shelf-life of the solution in the sealed original packaging may be 1 month or more, in particular between 1 month and 24 months, but at least between 1 month and 18 months, preferably between 1 month and 12 months, more preferably between 1 month and 9 months, most preferably between 1 month and 6 months, particularly between 1 month and 3 months. Details of the stability tests by way of example can be found in Tables 1 and 2 which follow:

Test of Stability after Opening

Packing material: 50 mL colorless glass vials, glass type I, ethylenepropylenenorbornene terpolymer rubber stopper (Type: WI 640 grey), aluminium flanged cap.

Recipe: analogous to Example 1 of the description 4 mL samples were taken from the storage samples three times a day for six days and on the seventh day 4 mL samples were taken four times. Storage was then continued until 28 days had elapsed and samples were taken again.

TABLE 1

| Test No. | Storage conditions [° C./% relative humidity] | Storage time [Days] | Meloxicam content [mg/mL] |
| --- | --- | --- | --- |
| 1 | 25° C. | 0 | 19.7 |
|   | 25° C./60% | 28 | 19.2 |
| 2 | 25° C. | 0 | 20 |
|   | 25° C./60% | 28 | 19.2 |

In both samples, in addition to the meloxicam content, the parameters investigated, namely appearance (clear yellow solution), pH (8.0-9.7), ethanol content (13.5-15.75), disodium EDTA content (85.0-110.0 mg/100 mL), sterility (according to Pharm. Eur. and USP), and the stability of the packaging material were found to be unchanged.

Long Term Stability Test in Sealed Original Packaging

Packaging material: 50 mL colorless glass vials, glass type I, ethylenepropylenenorbornene terpolymer rubber stopper (Type: WI 640 grey), aluminium flanged cap.

Recipe: Analogous to Example 1 of the description.

TABLE 2

| Test No. | Storage conditions [° C./% relative humidity] | Storage time [Days] | Meloxicam content [mg/mL] |
|---|---|---|---|
| 1 | 25° C. | 0 | 19.7 |
|  | 4° C. | 6 | 19.9 |
|  | 40° C./75% | 6 | 19.5 |
|  | 25° C./60% | 18 | 19.3 |
|  | 30° C./70% | 18 | 19.4 |
| 2 | 25° C. | 0 | 20.0 |
|  | 4° C. | 6 | 19.9 |
|  | 40° C./75% | 6 | 19.7 |
|  | 25° C./60% | 18 | 19.4 |
|  | 30° C./70% | 18 | 19.5 |
|  | 25° C./60% | 24 | 19.5 |
|  | 30° C./70% | 24 | 19.5 |

In both samples, in addition to the meloxicam content, the parameters investigated, namely appearance (clear yellow solution), pH (8.0-9.7), ethanol content (13.5-15.75), disodium EDTA content (85.0-110.0 mg/100 mL), sterility (according to Pharm. Eur. and USP), and the stability of the packaging material were found to be unchanged.

The formulation according to the invention should have a pH of between 8 and 10, preferably between 8.5 and 9, more preferably a pH between 8.7 and 8.9, and particularly 8.8.

The formulation according to the invention is suitable for treating pain, inflammation, fever, acute mastitis, diarrhea, lameness, problems with the locomotor apparatus, and respiratory complaints in animals, preferably acute mastitis, diarrhea, lameness, problems with the locomotor apparatus and respiratory complaints, especially acute mastitis, diarrhea, lameness, problems with the locomotor apparatus and respiratory complaints, and most preferably respiratory complaints. The treatment may be given in conjunction with antibiotic therapy.

The formulation according to the invention is suitable for treating animals, preferably farm animals, and more particularly large farm animals.

The formulation according to the invention is suitable for treating animals, preferably animals up to 500 kg, particularly large animals up to 750 kg.

The dosage of the formulation according to the invention should corresponding to 0.2 to 1.0 mg of active substance per kg of bodyweight, preferably 0.4 to 0.8 mg/kg of bodyweight, more preferably 0.5 to 0.7 mg/kg of bodyweight, and particularly preferably 0.6 mg/kg of bodyweight.

The formulation according to the invention may be prepared using the methods of preparing aqueous liquid formulations known from the literature. For example, the appropriate excipients may be added to a meloxicam salt solution.

Various commercial materials for aqueous liquid formulations which will allow sealing under inert gas and final sterilization by autoclaving in the finished container may be used as a packaging material for the formulation according to the invention. Such materials include for example ampoules or glass vials, particularly glass vials, e.g., 50 mL or 100 mL glass vials of glass Type I (according to Pharm. Eur/USP) in conjunction with rubber stoppers made of ethylenepropylenenorbornene terpolymer (Type WI 640 grey) and aluminium caps.

The meloxicam solutions according to the invention will now be illustrated by the Examples which follow. Anyone skilled in the art will be aware that the Examples serve only as an illustration and are not to be regarded as restrictive.

Examples

| Example 1: 2% Meloxicam Solution | |
|---|---|
| Component | Amount (g/L) |
| Meloxicam | 20.0 |
| Meglumine | 14.0 |
| Macrogol 300[1] | 150.0 |
| Poloxamer 188[2] | 50.0 |
| Ethanol | 150.0 |
| Glycine | 5.0 |
| EDTA-Na | 1.0 |
| 1 M HCl | q.s. ad pH 8.8 |
| 1 M NaOH | q.s. ad pH 8.8 |
| Water for injections | ad 1000 mL |

Legend: [1]obtainable from Brenntag, Plochingen, Germany; and [2]obtainable from C.H. Erbsloeh, Krefeld, Germany Method:

20 g of meloxicam are dissolved in 500 mL of an aqueous meglumine solution (14 g/500 mL) at 90° C. The other excipients are added one after another to the solution according to the recipe given above. A pH of 8.8 is then achieved using 1M hydrochloric acid and 1M sodium hydroxide solution. Water is added to the solution until a volume of 1 liter is obtained.

| Example 2: 2% Meloxicam Solution | |
|---|---|
| Component | Amount (g/L) |
| Meloxicam | 20.0 |
| Meglumine | 12.5 |
| PEG 400 | 100.0 |
| Poloxamer | 50.0 |
| Ethanol | 150.0 |
| Glycine | 5.0 |
| EDTA-Na | 1.0 |
| 1 M HCl | q.s. ad pH 8.8 |
| 1 M NaOH | q.s. ad pH 8.8 |
| Water for injections | ad 1000 mL |

Method:

20 g of meloxicam are dissolved in 500 mL of an aqueous meglumine solution (12.5 g/500 mL) at 90° C. The other excipients are added one after another to the solution according to the recipe given above. A pH of 8.8 is then achieved using 1M hydrochloric acid or 1M sodium hydroxide solution. Water is added to the solution until a volume of 1 liter is obtained.

| Example 3: 2.5% Meloxicam Solution | |
|---|---|
| Component | Amount (g/L) |
| Meloxicam | 25.0 |
| Meglumine | 17.5 |
| PEG 300 | 150.0 |
| Poloxamer | 50.0 |
| Ethanol | 150.0 |
| Glycine | 5.0 |
| EDTA-Na | 1.0 |
| 1 M HCl | q.s. ad pH 8.8 |
| 1 M NaOH | q.s. ad pH 8.8 |
| Water for injections | ad 1000 mL |

Method:

25 g of meloxicam are dissolved in 500 mL of an aqueous meglumine solution (17.5 g/500 mL) at 90° C. The other excipients are added one after another to the solution according to the recipe given above. A pH of 8.8 is then achieved using 1M hydrochloric acid or 1M sodium hydroxide solution. Water is added to the solution until a volume of 1 liter is obtained.

Example 4: 1.5% Meloxicam Solution

| Component | Amount (g/L) |
|---|---|
| Meloxicam | 15.0 |
| Meglumine | 10.5 |
| PEG 300 | 100.0 |
| Poloxamer | 50.0 |
| Ethanol | 150.0 |
| Glycine | 5.0 |
| EDTA-Na | 1.0 |
| 1 M HCl | q.s. ad pH 8.8 |
| 1 M NaOH | q.s. ad pH 8.8 |
| Water for injections | ad 1000 mL |

Method:

15 g of meloxicam are dissolved in 500 mL of an aqueous meglumine solution (10.5 g/500 mL) at 90° C. The other excipients are added one after another to the solution according to the recipe given above. A pH of 8.8 is then achieved using 1M hydrochloric acid or 1M sodium hydroxide solution. Water is added to the solution until a volume of 1 liter is obtained.

Example 5: 2% Meloxicam Solution

| Component | Amount (g/L) |
|---|---|
| Meloxicam | 20.0 |
| Meglumine | 14.0 |
| PEG 300 | 150.0 |
| Poloxamer | 50.0 |
| p-Chloro-m-cresol | 2.0 |
| Glycine | 5.0 |
| EDTA-Na | 1.0 |
| 1 M HCl | q.s. ad pH 8.8 |
| 1 M NaOH | q.s. ad pH 8.8 |
| Water for injections | ad 1000 mL |

Method:

20 g of meloxicam are dissolved in 500 mL of an aqueous meglumine solution (14 g/500 mL) at 90° C. The other excipients are added one after another to the solution according to the recipe given above. A pH of 8.8 is then achieved using 1M hydrochloric acid or 1M sodium hydroxide solution. Water is added to the solution until a volume of 1 liter is obtained.

What is claimed:

1. A treatment method for treating non-human a mammal suffering from one or more of pain, inflammation, fever, acute mastitis, diarrhea, lameness, locomotor deficiency, or respiratory illness, the method comprising administering to the mammal an aqueous, cyclodextrin-free solution, the solution comprising:
   meloxicam in an amount of 20 mg/ml;
   meglumine in an amount of 14 mg/ml;
   a polyethylene glycol in an amount of 150 mg/ml;
   a polyoxyethylene-polyoxypropylene copolymer in an amount of 50 mg/ml;
   ethanol in an amount of 150 mg/ml;
   glycine in an amount of 5 mg/ml;
   disodium EDTA in an amount of 1 mg/ml;
   hydrochloric acid and/or sodium hydroxide provided in an amount sufficient to yield a pH of 8.8 of the solution; and
   water.

2. The method according to claim 1, wherein the method is used in conjunction with antibiotic therapy.

3. The method according to claim 1, wherein the mammal is a large animal having a body weight greater than 500 kg and up to 750 kg.

4. A treatment method for treating a non-human animal suffering from one or more of pain, inflammation, fever, acute mastitis, diarrhea, lameness, locomotor deficiency, or respiratory illness, the method comprising administering to the animal an aqueous, cyclodextrin-free solution, the solution consisting of:
   meloxicam in an amount of 20 mg/ml;
   meglumine in an amount of 14 mg/ml;
   a polyethylene glycol in an amount of 150 mg/ml;
   a polyoxyethylene-polyoxypropylene copolymer in an amount of 50 mg/ml;
   ethanol in an amount of 150 mg/ml;
   glycine in an amount of 5 mg/ml;
   disodium EDTA in an amount of 1 mg/ml;
   hydrochloric acid and/or sodium hydroxide provided in an amount sufficient to yield a pH of 8.8 of the solution; and
   water.

* * * * *

UNITED STATES PATENT AND TRADEMARK OFFICE
CERTIFICATE OF CORRECTION

PATENT NO. : 9,956,288 B2  
APPLICATION NO. : 15/297594  
DATED : May 1, 2018  
INVENTOR(S) : Stefan Henke et al.

Page 1 of 1

It is certified that error appears in the above-identified patent and that said Letters Patent is hereby corrected as shown below:

In the Claims

Claim 1, (Line 5, Column 8) "A treatment method for treating non-human a mammal" should read "A treatment method for treating a non-human mammal"

Signed and Sealed this  
Eighteenth Day of September, 2018

Andrei Iancu  
*Director of the United States Patent and Trademark Office*